(12) United States Patent  
Brugidou et al.

(10) Patent No.: US 9,222,097 B2  
(45) Date of Patent: Dec. 29, 2015

(54) FUNCTIONAL VIRAL VECTORS FOR THE OVEREXPRESSION OR EXTINCTION OF PARTICULAR GENES IN PLANTS, AND APPLICATIONS THEREOF

(75) Inventors: Christophe Brugidou, Pignan (FR); Christelle Sire, Barcelona (ES)

(73) Assignee: INSTITUT DE RECHERCHE POUR LE DEVELOPPEMENT (IRD), Marseilles (FR)

( * ) Notice: Subject to any disclaimer, the term of this patent is extended or adjusted under 35 U.S.C. 154(b) by 1535 days.

(21) Appl. No.: 11/794,759

(22) PCT Filed: Jan. 5, 2006

(86) PCT No.: PCT/FR2006/000017  
§ 371 (c)(1),  
(2), (4) Date: Nov. 20, 2007

(87) PCT Pub. No.: WO2006/072742  
PCT Pub. Date: Jul. 13, 2006

(65) Prior Publication Data  
US 2009/0162832 A1    Jun. 25, 2009

(30) Foreign Application Priority Data  
Jan. 5, 2005    (FR) .................................... 05 00090

(51) Int. Cl.  
*C12Q 1/70* (2006.01)  
*C12N 7/01* (2006.01)  
*C12N 15/82* (2006.01)

(52) U.S. Cl.  
CPC ........ *C12N 15/8203* (2013.01); *C12N 15/8218* (2013.01)

(58) Field of Classification Search  
None  
See application file for complete search history.

(56) References Cited

FOREIGN PATENT DOCUMENTS

| WO | 00/79001 | 12/2000 |
|---|---|---|
| WO | 01/38512 | 5/2001 |
| WO | 02/057301 | 7/2002 |
| WO | 02/057467 | 7/2002 |

OTHER PUBLICATIONS

International Search Report for PCT/FR2006/000017 mailed Sep. 28, 2006.  
Vionnet et al., "Suppression of gene silencing: A general strategy used by diverse DNA and RNA viruses of plants," Proceedings of the National Academy of Sciences, vol. 96, No. 24, Nov. 23, 1999, pp. 14147-14152, XP002174430.  
Hou et al., "A novel co-delivery system consisting of a *Tomato bushy stunt virus* and a defective interfering RNA for studying gene silencing," Journal of Virological Methods, vol. 111, No. 1, Jul. 2003, pp. 37-42, XP002324218.  
Fargette et al, "Rice yellow mottle virus complete genome, isolate Tz3", Accession No. AJ608216, http://www.ncbi.nlm.nih.gov (printed Apr. 18, 2012).  
Fargette et al, "Rice yellow mottle virus complete genome, isolate Mg2", Accession No. AJ608211, http://www.ncbi.nlm.nih.gov. (printed Apr. 18, 2012).

(Continued)

*Primary Examiner* — Nancy Treptow Vogel  
(74) *Attorney, Agent, or Firm* — Young & Thompson

(57) ABSTRACT

The invention relates to the use of genes which, in plants, encode proteins with a functional diversity in terms of silencing, comprising the selection of the gene with the level of effectiveness in order to construct a plant viral vector having the function of overexpressing or silencing particular genes.

6 Claims, 11 Drawing Sheets

(56) References Cited

OTHER PUBLICATIONS

Fargette et al, "Rice yellow mottle virus complete genome, isolate Tz8", Accession No. AJ608218, http://www.ncbi.nlm.nih.gov (printed Apr. 18, 2012).

Fargette et al, "Rice yellow mottle virus complete genome, isolate Cl63", Accession No. AJ608207, http://www.ncbi.nlm.nih.gov (printed Apr. 18, 2012).

Fargette et al, "Inferring the Evolutionary History of *Rice Yellow Mottle Virus* from Genomic, Phylogenetic, and Phylogeographic Studies", Journal of Virology, Apr. 2004, vol. 78, No. 7, pp. 3252-3261.

-a-

-b-

SEQUENCE LISTING

```
<160> NUMBER OF SEQ ID NOS: 23

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgtactagt gggc                                                        14

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acaaagatgg ccaggaaggg caag                                             24

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

-continued

```
gaattctacg tatcacgtat tgagtgttgg atc                                    33

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaattcacta gtgtgagcaa gggcgagga                                         29

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaattcacta gtttacttgt acagctcgtc cat                                    33

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattcacta gtttacgtcc tgtagaaacc                                        30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaattcacta gttcattgtt tgcctccctg                                        30

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acaaagatgg ccaggaaggg caag                                              24

<210> SEQ ID NO 9
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```

```
gaattctacg tagcatgcca tctttgtggg agactcgccc tatcccactc acgtattgag    60
tgttggatc                                                            69
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gaattcgcat gcgtgagcaa gggcgaggag                                     30
```

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gaattcgcat gcttacttgt acagctcgtc cat                                 33
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
gaattctacg tagcacgact tctt                                           24
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gaattctacg tagcacgact tctt                                           24
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gaattctacg tacggcatca a                                              21
```

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
gaattctacg tacgccgccg ggat                                          24
```

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 16

```
gaattctacg taatagaact taatcct                                       27
```

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

```
gaattctacg tacctggacg tagc                                          24
```

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 18

```
gaattctacg tacgggcgcg ggact                                         25
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 19

```
gaattctacg tagcacgctg ccgt                                          24
```

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 20

```
gaattctacg tattgtacag ctcg                                          24
```

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 21

```
<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctcccccacc catcccgaga                                                     20

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaattcactg tgagcaaggg cgagga                                              26
```

FUNCTIONAL VIRAL VECTORS FOR THE OVEREXPRESSION OR EXTINCTION OF PARTICULAR GENES IN PLANTS, AND APPLICATIONS THEREOF

This application is the US national phase of international application PCT/FR2006/000017 filed 5 Jan. 2006, which designated the U.S. and claims benefit of FR 0500090 filed 5 Jan. 2005, the entire contents of each of which are hereby incorporated by reference.

FIELD OF THE INVENTION

The invention relates to functional viral vectors for the overexpression, or for the post-transcription extinction (hereinafter referred to as "silencing") of genes of interest in plants. It relates more particularly to vectors generated from plant viruses and which comprise sequences encoding proteins with a functional diversity in terms of the overexpression or silencing of genes in cereals, in particular in rice.

BACKGROUND OF THE INVENTION

One of the main antiviral defense mechanisms in plants, and also in animals, is based on the phenomenon of PTGS (post-transcriptional gene silencing) which results in the specific degradation of foreign or overexpressed RNAs.

In the case of viruses, the viral genome is the triggering agent and the target of the phenomenon.

Concomitantly, viruses have developed functions which allow them to bypass this type of defense mechanism, by specializing some of their proteins in silencing suppressor functions which target key steps of PTGS.

Many proteins, referred to as "silencing suppressors" have been described in phytopathogenic viruses by virtue of non-host interactions for some of them in *Nicotiana benthamiana*. In fact, PVX-potential suppressor protein vectors have been generated and inoculated (by agroinfiltration) onto *N. benthamiana* plants exhibiting PTGS in order to evaluate the suppressor capacity of the proteins studied. The P1 protein of the rice yellow mottle sobemovirus (hereinafter referred to as "RYMV"), a virus exclusively restricted to the infection of rice and some wild-type grasses, has thus been described as a silencing suppressor.

The P1 protein of RYMV is a protein of 158 amino acids encoded by the first of the 4 viral ORFs. This protein is translated during the entire infectious cycle and detected in the form of a doublet of 18 and 19 kDa. It exerts an indirect action on viral replication and appears to be necessary for the movement of RYMV from cell to cell and for long distance movement. Complementation studies have shown that it acts in trans during viral infection. This protein has been described as a silencing suppressor that acts in the "nonautonomous" cell mode and therefore on the propagation of the PTGS signal.

The inventors have evaluated the effectiveness of the P1 protein and of RYMV in suppressing PTGS in a context of natural interaction between RYMV and its host, rice.

The studies carried out on a collection of RYMV isolates, characterized in terms of pathology and phylogeny, have made it possible to demonstrate P1 diversity and functional differences in activity which are related to this diversity. These studies have also made it possible to explore the quantitative and qualitative effects of these P1s and RYMV on PTGS suppression.

SUMMARY OF THE INVENTION

The aim of the invention is therefore to take advantage of the functional diversity of silencing suppressors in order to provide new viral expression or silencing vectors and functional genomic tools based on the functional diversity of a suppressor protein of a plant virus.

The invention is also aimed at providing viral expression and VIGS (virus induced gene silencing) vectors and the construction thereof from plant viruses, and more particularly from RYMV, for the purpose of providing effective tools for functional genomic in rice, a model plant for monocotyledons.

DETAILED DESCRIPTION OF THE INVENTION

According to a first aspect, the invention therefore relates to the use of genes encoding, in plants, proteins with a functional diversity in terms of silencing, and the selection of the gene having the level of effectiveness in order to construct a plant viral vector having the function of overexpressing or silencing genes of desired interest.

The invention also relates to the use of genes encoding, in plants, P1 proteins of RYMV, with weak-to-strong suppressor effects according to the proteins, in order to construct functional plant viral vectors for overexpressing or silencing genes of interest.

The invention is directed more particularly toward the use of proteins selected for a given level of activity using a technique comprising
  cloning silencing suppressor proteins with a functional diversity downstream of an appropriate promoter, such as the RYMV 35S promoter,
  inoculating the various proteins by biolistics onto rice leaves,
  mechanically inoculating virus onto lines, such as the L2,4 and L10 lines,
  assaying the viral load by DAS-ELISA using a polyclonal antibody directed against a given isolate, for example a Madagascar isolate,
  visualizing the restoration of the expression of the reporter gene by means of a GUS histochemical assay,
  quantifying the restoration of the expression of the reporter gene by assaying the enzymatic activity,
  detecting the siRNAs (evidence of PTGS) by Northern blotting, and
  selecting the protein having the level of activity required for either overexpressing or silencing a gene of interest.

For the selection of P1 proteins, the above technique is applied by cloning the various P1s, more particularly Tz3, Tz8, Mg1, BF1, Ci63, downstream of the 35S promoter.

Preferably, the sP1-Ci63 and Tz3 proteins are used for high effectiveness in PTGS suppression. P1 proteins such as sP1-Tz8 exhibit an intermediate effectiveness, whereas s-P1Mg1 and -BF1 are not very effective in PTGS suppression.

The results obtained, illustrated by the examples, show that the variability in PTGS suppression by the various P1 proteins is expressed both on the quantitative scale, the proteins showing a more or less substantial activity, but also on the qualitative scale, the results showing a differential rate of PTGS suppression.

The activity of the P1 proteins on PTGS suppression was evaluated by analyzing their effect on the accumulation of miRNAs and of siRNAs. It was found that the variable effectiveness of PTGS suppression results in a variable decrease in siRNAs specific for the transgenes tested. The analyses carried out also revealed that the P1 proteins bring about a decrease in miRNA accumulation.

The invention also relates to the use of the genome of an RYMV isolate, with a variable, strong-to-weak, PTGS suppressor effect.

According to another aspect, the invention relates to viral vectors for the expression or silencing of genes of interest, characterized in that they are generated from the RYMV genome and comprise a gene encoding a silencing suppressor chosen so as to have the level of effectiveness for defining the desired overexpression or silencing functionality.

The construction of such vectors supposedly takes into account all the constraints imposed by the structure of the virus and is tightly dependent on the abilities of the virus to conserve its infectious potential (with respect to movement and to encapsidation).

The invention is directed toward viral vectors for the expression or silencing of genes of interest, characterized in that they are generated from the RYMV genome and comprise a gene encoding P1 proteins which express a functional diversity as silencing suppressors. This gene replaces that of the RYMV genome encoding any P1 protein.

These vectors advantageously exhibit an intensity of replication equivalent to that of known infectious clones and induce the same symptoms.

In one embodiment, the vectors of the invention are characterized in that they are viral expression vectors containing an insert of a gene of interest to be overexpressed or to be extinguished, of less than 700 pb in size.

For insert sizes greater than 700 bp, use is made of the replicative ORF (i.e. $ORF_{2a,\ 2b}$) or "amplicon" of RYMV, which makes it possible to have sufficient space for the insertion of large sequences.

The absent ORFs may be complemented in trans (i.e. transgenic plants) or in cis (i.e. coinoculation).

These viral expression vectors are good candidates as tools for the transient expression of genes.

Advantageously, they have a sequence with restriction sites of interest for the cloning of exogenous sequences.

These vectors are also characterized in that they additionally comprise a gene encoding the p19 PTGS suppressor, in order to make the clone more functional in non-host cells, such as BY2 protoplasts.

In another embodiment, the vectors of the invention are characterized in that they are VIGS vectors containing inserts of less than 50 pb in size, whatever their orientation of insertion in the viral genome, and the target of which is the mRNA of the transgene.

The vectors defined above are advantageously obtained according to a protocol comprising the steps of:
  PCR amplification;
  digestion;
  ligation;
  transformation of competent bacteria.
The expression vectors are validated more particularly according to a protocol comprising the steps of
  in vitro transcription;
  preparation and electroporation of protoplasts with the transcripts;
  visualization of the inserts 3 to 7 days after electroporation;
  extraction of RNA according to the same timing;
  validation of the replication and stability of the inserted genes by RT-PCR.
The VIGS vectors are more especially validated according to a protocol comprising the steps of:
  in vitro transcription;
  mechanical inoculation of various rice varieties with variable degrees of resistance to RYMV, and transgenic lines, with the transcripts;
  phenotypic characterization with visualization of the silencing phenotypes;
  molecular characterization with the extraction of total RNA, polyacrylamide gel Northern blotting of the low-molecular-weight RNAs and detection of the siRNAs specific for the genes targeted by VIGS.

The invention thus provides tools of great interest for the insertion of exogenous genes into the RYMV genome for the purpose of overexpressing them or silencing them.

The study of PTGS suppression by RYMV has made it possible to demonstrate the importance of the amount of virus inoculated.

The construction and the validation of the viral expression and VIGS vectors make it possible to develop a set of tools suitable for studying gene expression and for producing molecules of interest, transiently in rice (production of proteins in rice protoplasts by electroporation, in cell suspensions of rice by coculture with *agrobacteria* such as *A. tumefaciens*, transient expression on leaves by bombardment). On the tissue scale, inoculation of rice leaves by biolistics makes it possible to carry out functional complementation studies.

The results obtained in accordance with the invention on PTGS suppression by the P1 proteins and by RYMV as a whole allow better targeting of the use of the vectors.

A P1 protein, or a combination of suppressors, with weak PTGS suppression activity will constitute an ideal tool for the creation of VIGS vectors. On the other hand, a strong PTGS suppression activity will be exploited for the optimization of expression vectors.

Other features and advantages of the invention are given in the examples which follow and FIGS. 1 to 12, which represent, respectively,

The controls correspond to 4 NI, the L4 transgenic line constitutively expressing the uida transgene and L10 NI/BI, the L10 transgenic line with uida constitutively extinguished, respectively non-inoculated and inoculated with a buffer. The enzymatic activity was also measured in the leaves using plants inoculated with the virus (i.e. L10 line with gus extinction) categorized according to the intensity of apparent symptoms (from class I to V) at 30 dai. a—results following viral inoculation under standard inoculation conditions (H$_c$I); b—results following viral inoculation under weak inoculation conditions (L$_c$I).

Figure 3:
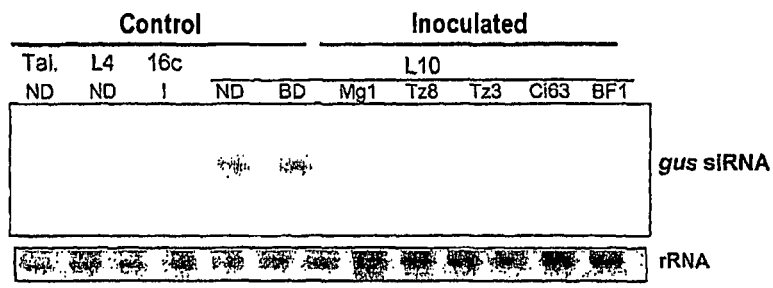

FIG. 3: Quantitative effect of various P1s on gus-specific SiRNAs: Northern blotting experiments for the detection of 2-day gus-specific siRNAs with biolistics of various s-P1 of RYMV isolates representative of the phylogeny of the virus (sP1-Mg1, -Tz3, -Tz8, -Ci63). The detection of the siRNAs is carried out on the total RNA extracted from leaves of the rice cultivar Taipei, or the transgenic rice line L4 with constitutive expression of the gus transgene, the *N. benthamiana* 16c line (16c) and the transgenic rice line L10 with constitutive extinction of the gus transgene. The rice leaves are analyzed after various treatments: intact leaf (ND for not delivered), injured leaf (BD for delivery of buffer by biolistics) and leaf inoculated with sP1-Mg1, -Tz8, -Tz3, -Ci63, -BF1 (Mg1, Tz8, Tz3, Ci63, BF1) by biolistics. The 16c leaves are infiltrated (I) with an *A. tumefaciens* strain carrying a binary plasmid with a Gus intron for the transient induction of PTGS on the uidA gene, and are analyzed 5 days after infiltration. Ethidium bromide staining of rRNA serves as a control.

Figure 4:
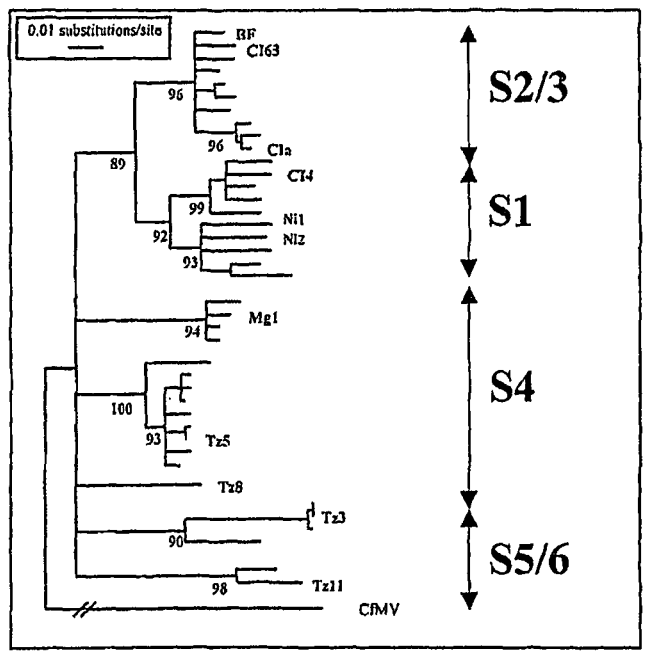

FIG. 4: Relationship tree for the various RYMV isolates. The phylogenetic tree is constructed according to the Neighbor-Joining method based on the alignment of the nucleic sequences of the ORF$_3$ encoding the capsid protein (CP) of the various isolates. The isolates used for the various analyses are highlighted in gray. Membership of various serogroups is indicated on the right of the tree.

Figure 5:
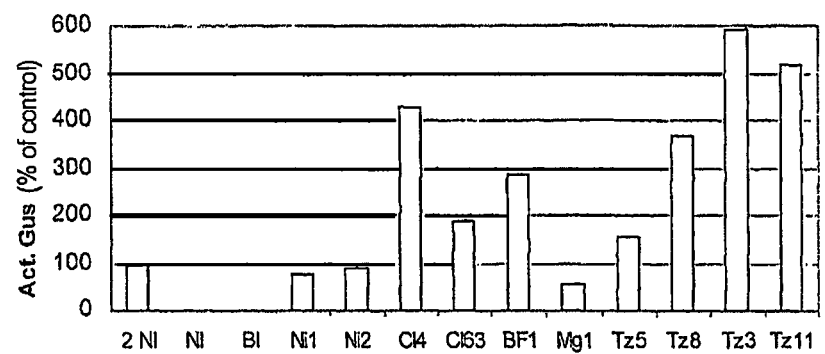

FIG. 5: Quantitative study of the lifting of PTGS as a function of the various isolates. Results of enzymatic assays for Gus activity (Act. Gus) carried out on proteins of leaves systemically infected with the isolates whose names are reported on the x-axis of the diagrams, and harvested at 35 dai. The level of restoration of the enzymatic activity is expressed as a percentage of the enzymatic activity of the reference L4 line as expected activity level. The controls consist of the assaying of Gus activity on the proteins extracted from leaves of the L4 line not inoculated (NI) and of the line not inoculated and inoculated with buffer (BI). Restoration of enzymatic activity, all isolates included.

Figure 6:
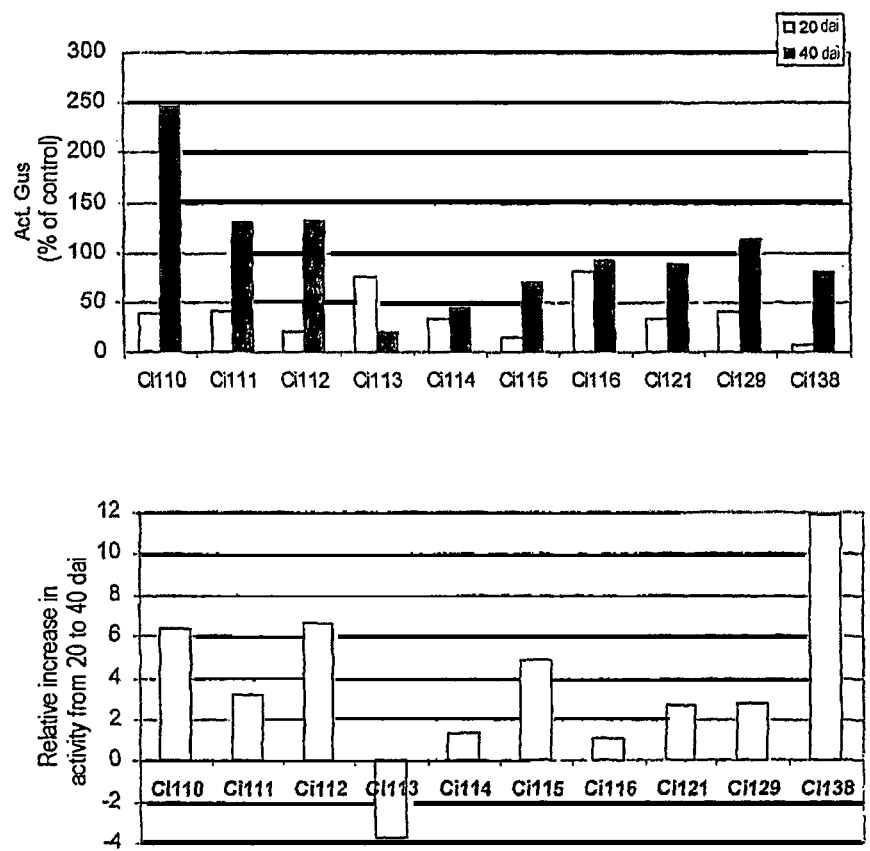

FIG. 6: Quantitative and qualitative study of the lifting of PTGS as a function of the various isolates of serogroup 2 in response to a controlled inoculation. Comparison of the results of enzymatic assays for Gus activity at 20 and 40 dai after inoculation. The lower diagram represents the relative variation in restoration of enzymatic activity between 20 and 40 days.

Figure 7:
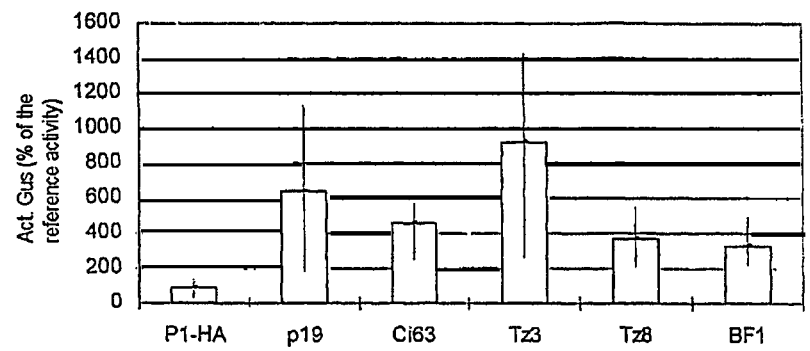
Figure 7:
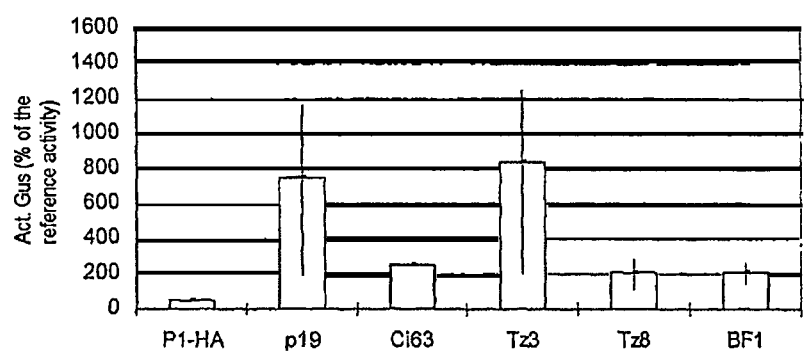
Figure 7:
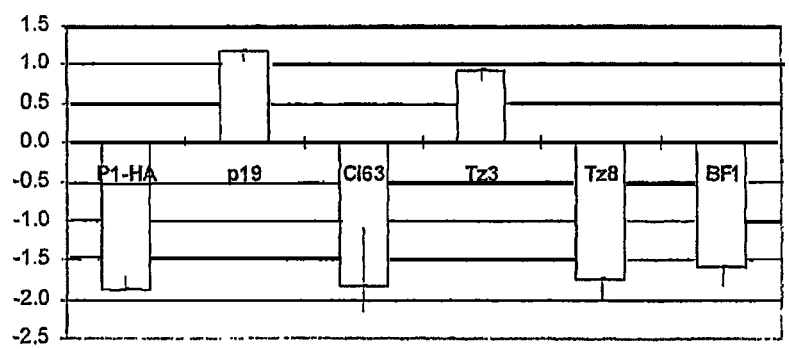

FIG. 7: Quantitative evaluation of the specific effect of the P1 of the various isolates representative of the phylogeny of the virus, on PTGS. a—results of the enzymatic assay for Gus activity carried out on proteins from *N. benthamiana* leaves coinfiltrated with *A. tumefaciens* strains containing pCambia1305.1 (Gus) and various constructs pBin-p19, pBin-P1-HA and bin-P1 the names of which are reported on the x-axis of the diagrams, and harvested at 3 and 4 dai. The level of restoration of the enzymatic activity is expressed as a percentage of the enzymatic activity of the leaves infiltrated with pCambia1305.1 alone as reference activity. For each P1 protein, three independent samples were analyzed and the standard deviation of the readings is represented on the diagram by bars. b—comparison of the results of enzymatic assays for Gus activity at 3 and 4 dai, and representation of the relative variation in the reinforcement of the enzymatic activity relative to a reference level between 3 and 4 dai.

Figure 8:
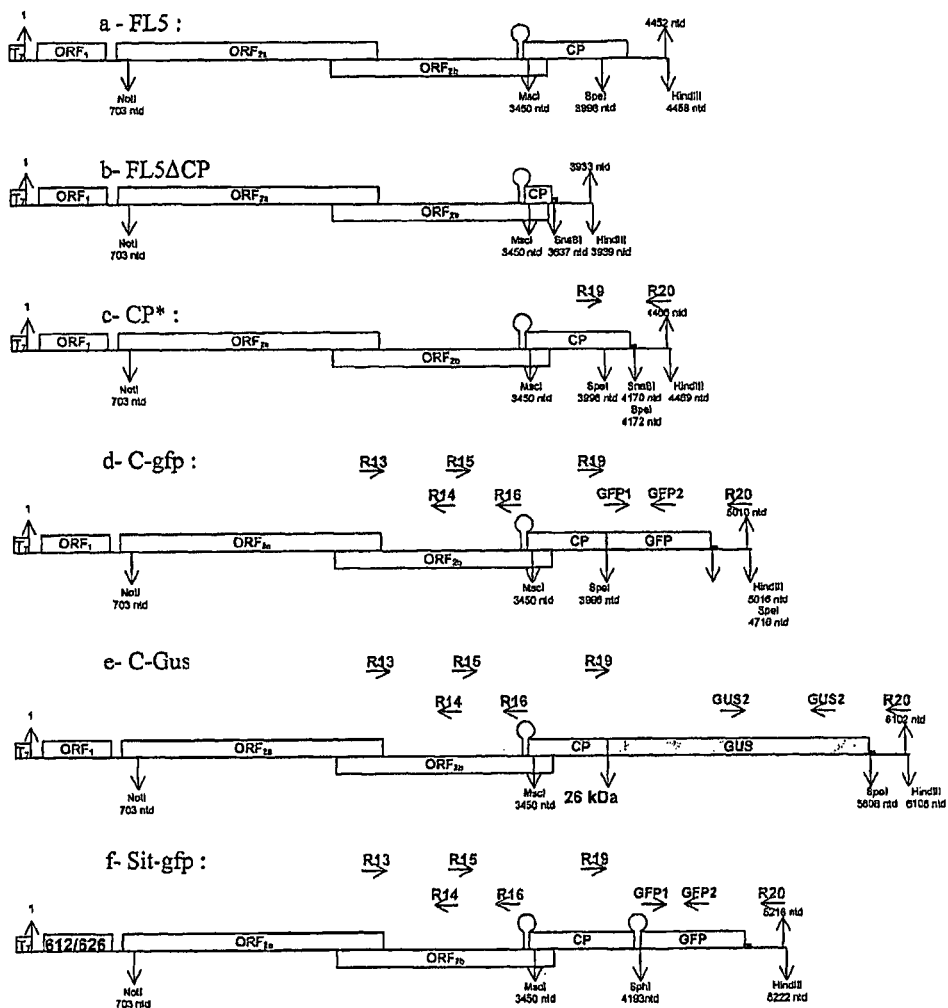

FIG. 8: The various infectious clones used and viral vectors generated: corresponds to the subgenomic RNA promoter, corresponds to 14 additional nucleotides (ACG TAC TAG TGGGC) (SEQ ID NO: 1). The position and the name of the various restriction sites used for the clonings are represented on the viral genome by descending arrows. The position and the name of the primers used for validating the vectors by RT-PCR are indicated with arrows.

Figure 9:
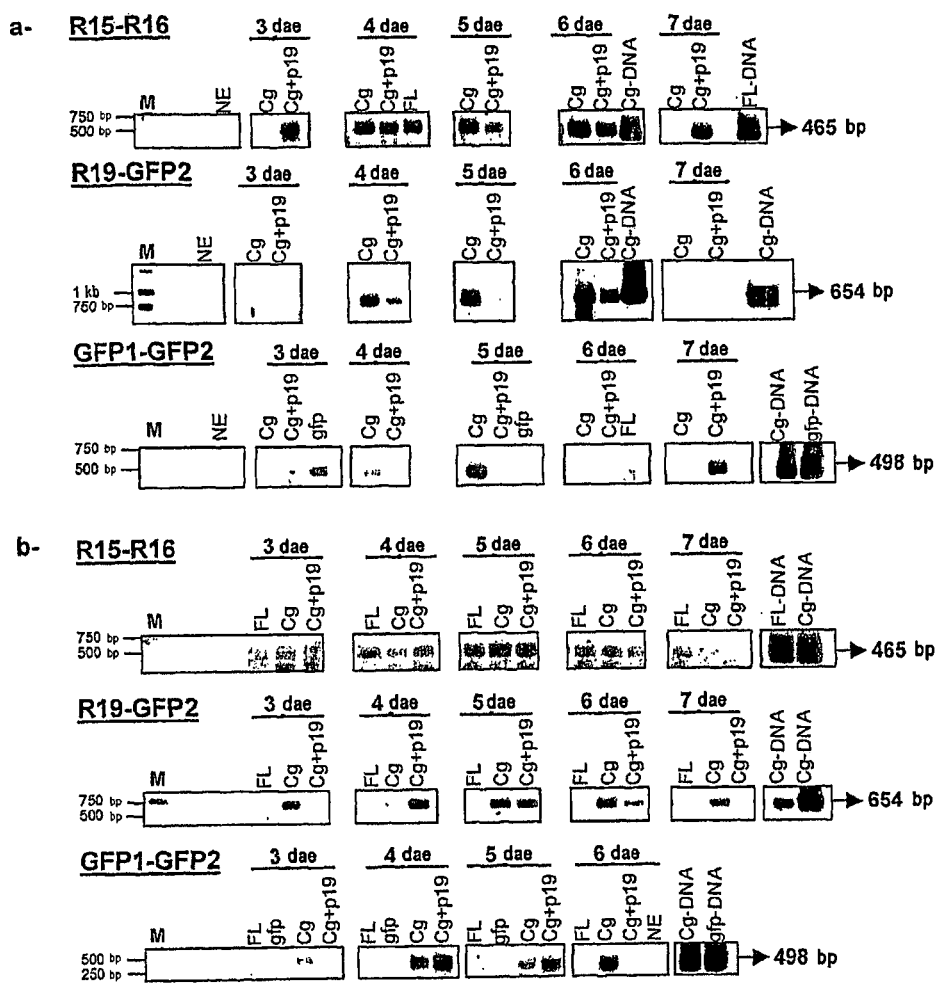

FIG. 9: Study of clone C-gfp, a—in BY2 protoplasts and b—in O$_{2428}$ protoplasts. Results of RT-PCR carried out on RNAs of protoplasts electroporated and harvested at 2, 3, 4, 5, 6, and 7 dae. Various electroporation conditions were analyzed and the protoplasts were nonelectroporated (NE), electroporated with in vitro transcripts of the C-gfp clone (Cg), electroporated with in vitro transcripts of the C-gfp clone and the plasmid p19 (Cg+p19), electroporated with the in vitro transcripts of the infectious clone FL5 (FL) and electroporated with the control plasmid 35S-gfp (gfp). Three PCR amplifications were carried out on the RT products, synthesized using the R20 primer, with the pairs of primers R15-R16, R19-GFP2 and GFP1-GFP2.

The lanes M, FL-DNA, Cg-DNA and gfp-DNA correspond respectively to the size marker and to the PCR amplifications carried out on the plasmid DNA of the FL5 and C-gfp clones and of 35S-gfp.

Figure 10:

FIG. 10: Study of the C-Gus clone, a—in BY2 protoplasts, b—in O$_{2428}$ protoplasts.

Results of RT-PCR carried out on RNAs of protoplasts electroporated and harvested at 2, 3, 4, 5, 6 and 7 dae. Various electroporation conditions were analyzed and the protoplasts were nonelectroporated (NE), electroporated with in vitro transcripts of the C-Gus clone (CG), electroporated with in vitro transcripts of the C-Gus clone and the plasmid p19 (CG+p19), electroporated with the in vitro transcripts of the infectious clone FL5 (FL), and electroporated with the control plasmid 35S-Gus (Gus). Three PCR amplifications were carried out on the RT products, synthesized using the R20 primer, with the pairs of primers R15-R16, R19-GUS2 and GUS1-GUS2.

The lanes M, FL-DNA, CG-DNA and Gus-DNA correspond respectively to the size marker and to the PCR amplifications carried out on the plasmid DNA of the FL5 and C-Gus clones and of the 35S-Gus control.

Figure 11:
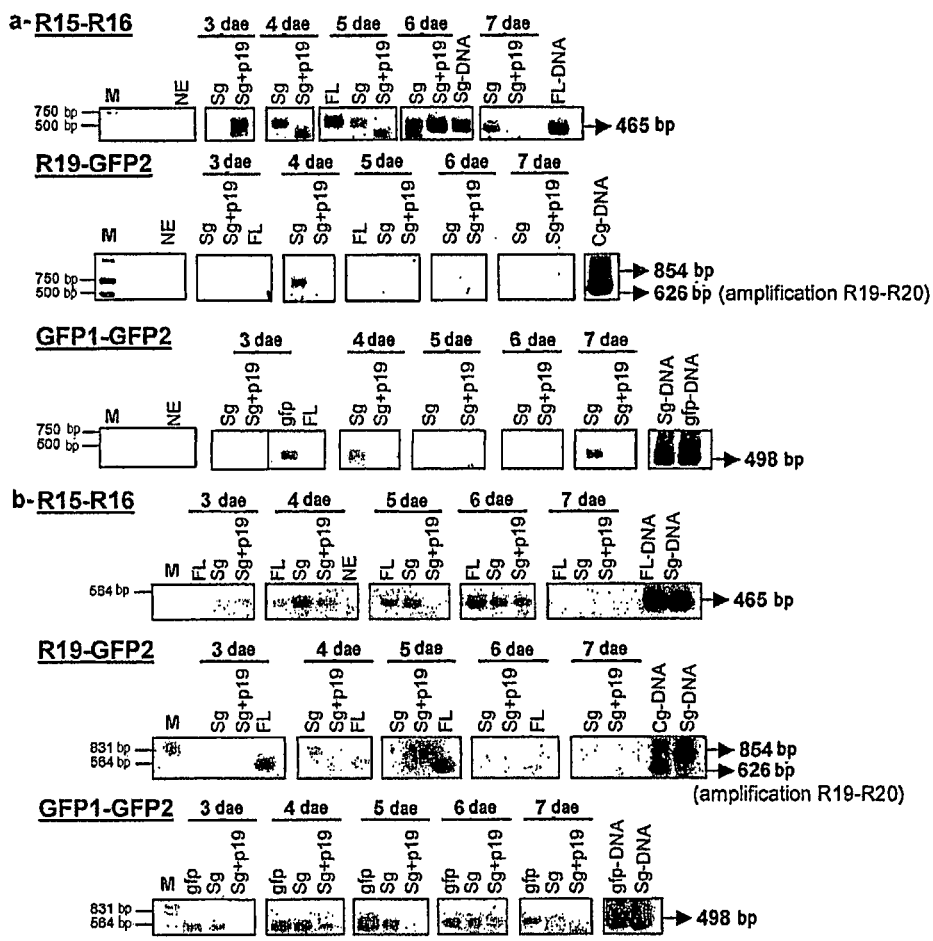

FIG. 11: Study of the Sit-gfp clone, a—in BY2 protoplasts, b—in O$_{2428}$ protoplasts. Results of RT-PCR carried out on RNAs of protoplasts electroporated and harvested at 2, 3, 4, 5, 6 and 7 dae. Various electroporation conditions were analyzed and the protoplasts were nonelectroporated (NE), electroporated with in vitro transcripts of the Sit-gfp clone (Sg), electroporated with in vitro transcripts of the Sit-gfp clone and the plasmid p19 (Sg+p19), electroporated with the in vitro transcripts of the infectious clone FL5 (FL), and electroporated with the 35S-gfp control plasmid (gfp). Three PCR amplifications were carried out on the RT products, synthesized using the R20 primer, with the pairs of primers R15-R16, R19-GFP2 and GFP1-GFP2. The amplifications of size less than the size expected with the R19-GFP2 primers correspond to an amplification with the primers R19 and R20 (residual primer of the RT).

The lanes M, FL-DNA, Sg-DNA and gfp-DNA correspond respectively to the size marker and to the PCR amplifications carried out on plasmid DNA of the FL5 and Sit-gfp clones and of the 35S-gfp control.

Figure 12:
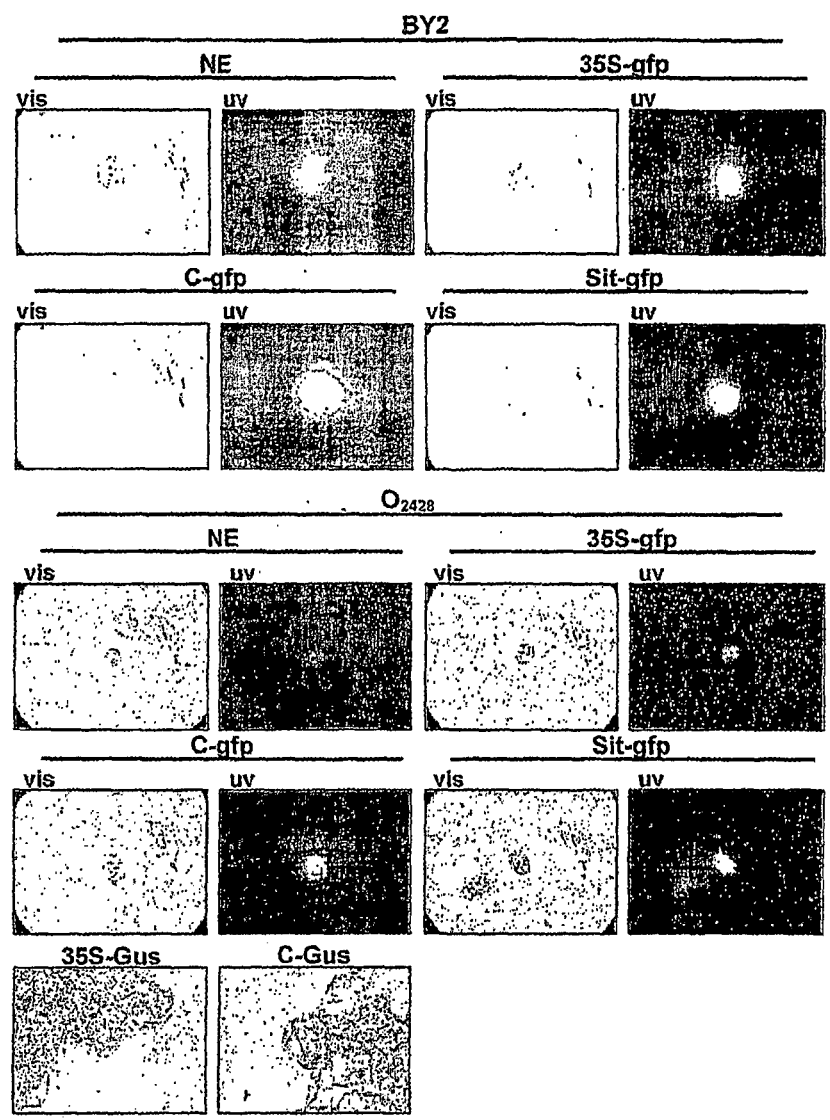

FIG. 12: Study of the expression of the reporter genes in *N. tabaccum* protoplasts (BY2) and *O. s.* protoplasts (O$_{2428}$) four days after electroporation with the in vitro transcripts generated from the various recombinants. For the recombinants expressing Gfp (C-gfp and Sit-gfp), the visualization of the protein was carried out under UV illumination (UV) after observation of the protoplasts under visible light (vis). The autofluorescence of the nonelectroporated protoplasts (NE) and also the fluorescence generated by the expression of the 35S-gfp control plasmid were evaluated and compared with that emitted in the protoplasts electroporated with the expression vectors.

The expression of Gus detected by histochemical assay in $O_{2428}$ protoplasts electroporated with the 35S-Gus control plasmid or the C-Gus recombinant was evaluated under visible light.

MATERIALS AND METHODS

The present patent application uses the properties of biological material derived from various African countries. The invention will be applied in accordance with the agreements of the Rio convention on biodiversity (URL: biodiv[dot]org).

The P1 protein of several RYMV isolates originating from various African countries is used to obtain the overexpression or extinction of genes. The use of the P1 proteins of the isolates referenced in the table below is expressly targeted in the description and the claims.

Name, origin, year of sample obtained, and knowledge acquired on the rice yellow mottle sobemovirus (RYMV) isolates used in the patent "Vecteurs viraux pour la surexpression ou pour l'extinction de genes d'intérêt chez les plantes et leurs applications" ["Functional viral vectors for the overexpression or extinction of genes of interest in plants, and applications thereof"]; name and member research institute of the researchers involved.

| Isolates | Origin | Year sample taken | Acquired knowledge | Researcher | Research institute |
|---|---|---|---|---|---|
| BF1 | Burkina Faso | 1990 | partial sequence | Jean-Loup Notteghem | CIRAD |
| C163 | Ivory Coast | 1997 | entire sequence | Placide N'Guessan | CNRA |
| Mg1 | Madagascar | 1989 | entire sequence | Jean-Loup Notteghem | CIRAD |
| Tz3 | Tanzania | 1997 | entire sequence | Zakia Abubakar | ZARC |
| Tz8 | Tanzania | 1997 | entire sequence | Zakia Abubakar | ZARC |

Infectious Clones

Figure 1:
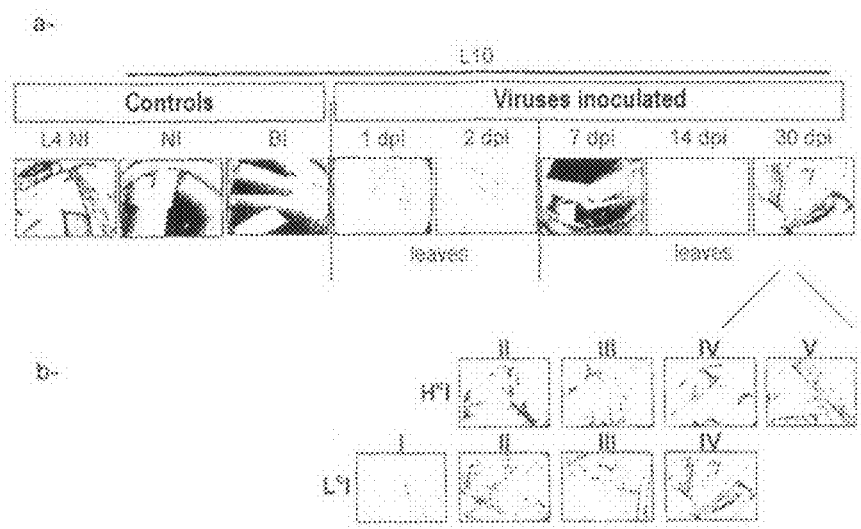
FIG. 1: Kinetics of restoration of Gus activity during viral infection from 1 to 30 days after inoculation (dai), in a transgenic line with gus extinction. a—the results of Gus histochemical staining in the rice leaves of various transgenic lines and with various inoculation conditions. The controls correspond to L4NI: L4 transgenic line constitutively expressing the uida transgene, and L10 NI/BI: L10 transgenic line with uida constitutively extinguished, not inoculated and inoculated with a buffer. The histochemical staining for Gus activity on leaves inoculated with viruses using L10 is controlled in the inoculated leaves at 1 and 2 days after inoculation and in leaves infected systemically at 7, 14 and 30 dai. The viral inoculation is carried out with a standard inoculum (condition $H^cI$). b—the results of the histochemical staining for Gus activity in infected leaves using L10 at 30 dai. For each independent inoculation condition ($H^cI$ or $L^cI$), the plants with a contrasted symptom intensity belonging to classes I to V are grouped together.
Figure 2:
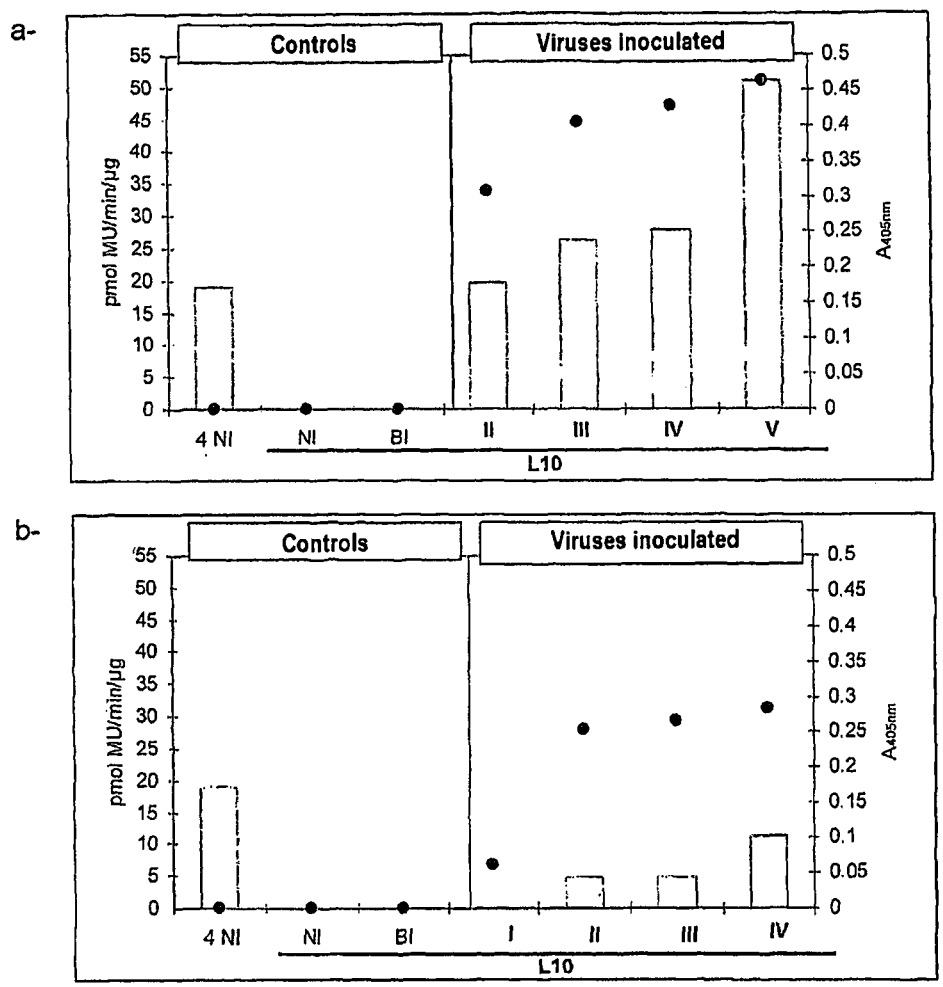
FIG. 2: Effect of the content of virus on silencing suppression by RYMV, revealed in leaves infected systemically using L10, harvested at 30 dai. Measurement of Gus activity by fluorimetry (expressed in pmol MU/min/μg protein and represented with shaded histograms) according to the content of virus evaluated by DAS-ELISA, the data corresponding to the absorbance ($A_{405nm}$) being represented by black dots.

The results obtained with the following infectious clones, which are illustrated in FIG. 1, are reported:
  FL5 (Brugidou et al, 1995), which corresponds to the complete cDNA of the viral genome cloned downstream of the T7 bacteriophage promoter;
  FL5ΔCP, from which a part of the ORF₃ encoding the capsid protein has been deleted (i.e. 3634 to 4167 nt), and which has 14 additional nucleotides in the 3' portion downstream of the deletion (ACG TAC TAG TGG GC) (SEQ ID NO: 1), corresponding to unique restriction sites advantageous for the insertion of supernumerary sequences;
  new clone CP*, constructed by insertion of a 720 bp fragment corresponding to the ORF of the CP amplified by 5'r PCR from FL5 (i.e. with the sense primer 5' ACA AAG ATG GCC AGG AAG GGC AAG 3' (SEQ ID NO: 2) and reverse primer 5' GAA TTC TACGTA TCA CGT ATT GAG TGT TGG ATC 3' (SEQ ID NO: 3), Tm 60° C.) and digested with MscI (in bold) and SnaBI (underlined), into FL5ΔCP digested with MscI (position 3450 nt) and SnaBI (position 3637 nt).

Expression Vectors

The viral expression vectors were generated from the recombinant CP*.

Fusions:

In a first step, transcriptional fusions by insertion of exogenous sequences at the SpeI site (positions 3996 to 4172 nt) were carried out, resulting in a partial deletion in the ORF of the CP corresponding to 54 amino acids in the protein. The complete sequences of the gfp+ gene (GenBank accession No. U84737) and of the uidA gene (GenBank accession No. AJ414112) were amplified with the oligonucleotides:
  gpf+ primers: sense 5' GAA TTC ACT GTGAGCAAGGGCGAGGA 3' (SEQ ID NO: 23), antisense 5' GAA TTC ACT AGT TTACTTGTACAGCTCGTCCAT 3' (SEQ ID NO: 5) (Tm 62° C.);
  uidA primers: sense 5' GAA TTC ACT AGT TTACGTCCTGTAGAAACC 3' (SEQ ID NO: 6), antisense 5' GAA TTC ACT AGT TCATTGTTTGCCTCCCTG 3' (SEQ ID NO: 7) (Tm 60° C.) (the sequences complementary to the sequences of the reporter genes are underlined). The PCR products (i.e. 720 bp for gpf+ and 1816 bp for uidA) were cloned at the SpeI site of CP* and the constructs thus produced are respectively called C-gfp and C-Gus.

Duplication of the Subgenomic RNA Promoter (SIT) (Hacker & Sivakumaraan, 1997):

The promoter is inserted into the 3' portion of the ORF of the CP by PCR amplification from FL5 with the sense primer 5' ACA AAG ATG GCC AGG AAG GGC AAG 3' (SEQ ID NO: 8) and antisense primer 5' GAA TTC TAC GTA GCA TGC CATCTTTGTGGGAGACTCGCCCTATCCCAC-TCACGTATTGAGTGTTGGATC 3' (SEQ ID NO: 9) (Tm 60° C.).

The SphI and SnaBI sites were also introduced by PCR in the position 5' of SIT (underlined). The 774 bp fragment thus amplified was introduced by ligation into FL5ΔCP at the MscI and SnaBI sites, and the clone generated was called C-Sit.

Cloning of gfp+ Downstream of SIT:

A 720 bp PCR fragment corresponding to the complete sequence of the gfp+ gene amplified with the sense primer 5' GAA TTC GCA TGC GTG AGC AAG GGC GAG GAG 3' (SEQ ID NO: 10) and antisense primer 5' GAA TTC GCA TGC TTA CTT GTA CAG CTC GTC CAT 3' (SEQ ID NO: 11), was cloned at the SphI site of C-Sit. This recombinant is denoted Sit-gfp.

VIGS Vectors

The VIGS vectors were generated by the insertion of PCR fragments of different sizes, from 44 to 121 bp, of the sgfp (GenBank accession No. U43284, AAC53659) (Pang et al, 1996; Sallaud et al, 2003) and pds (GenBank accession No.

AF049356) genes of O. sativa L. spp. indica cv. IR36, at the SnaBI site (position 4170 nt) of CP*. The results are given in table 1 below.

The inserts were not all integrated in the same orientation, "s" corresponds to the sense orientation and "as" to the antisense orientation. The inserts gf*, gf**, f* fp* and fp** were amplified using the primers specified in the table, from the DNA of the plasmid pCambia5305. The pds* insert was amplified by PCR in the presence of the appropriate primers, from a product of a reverse transcription reaction carried out on 750 ng of RNA extracted from leaves of rice cv. $IR_{64}$, in the presence of oligonucleotide primers of oligodT type.

Molecular Biology and Cell Culture Protocols

A) Analysis of PTGS Suppression

1a. Evaluation of Viral Load by DAS-ELISA

The viral content in the systemically infected leaves is estimated by enzymatic immunoassay according to the DAS-ELISA technique (Double Antibody Sandwich-Enzyme Linked ImmunoSorbent Assay).

One milliliter PBS-T (1.36M NaCl, 14 mM $KH_2PO_4$, 80 mM $Na_2HPO_4$, 26 mM KCl, pH 6.8, 0.5% v/v Tween 20) was added to 100 mg of powder derived from the ground, systemically infected leaves, thus constituting the antigen solution. Polyclonal antibodies (diluted to 1/1000th), derived from a

TABLE I

Tableau I

| Gene - name of vector | Position of the insert on the gene (insert size in bp) | Sense oligonucleotide 5'-3' | Antisense oligonucleotide 5'-3' | *Tm |
|---|---|---|---|---|
| Gfp - gf*as | 242-286 (44) | GAATTCTACGTAGCACGACTTCTT | GAATTCTACGTACCTGGACGTAGC | 55° C. |
| Gfp - gf**s | 242-334 (92) | GAATTCTACGTAGCACGACTTCTT | GAATTCTACGTACGGGCGCGGGACT | 55° C. |
| Gfp - f*as | 479-532 (53) | GAATTCTACGTACGGCATCAA | GAATTCTACGTAGCACGCTGCCGT | 57° C. |
| Gfp - fp*s | 677-716 (39) | GAATTCTACGTACGCCGCCGGGAT | GAATTCTACGTATTGTACAGCTCG | 55° C. |
| Pds - pds*s | 996-1071 (51) | GAATTCTACGTAATAGAACTTAATCCT | GAATTCTACGTATCCATCGGTAAG | 52° C. |

*Tm: average hybridization temperature of the two primers, used for the PCR amplifications
Table 1 discloses the "Sense" sequences as SEQ ID NOS 10-16 and the "Antisense" sequences as SEQ ID NOS 17-21, respectively, in order of appearance.

Validation

In vitro transcription of the recombinants

Expression Vectors

Electroporation

Approximately one million tobacco (Nicotiana tabaccum var BY2) or rice (O. sativa var $O_{2428}$, sensitive to RYMV) protoplasts were electroporated with 30 µg of in vitro transcripts corresponding to the expression vectors.

Seven independent electroporations were carried out for each recombinant vector and were mixed at the end of experiments.

VIGS Vectors

Mechanical Inoculation of Various Varieties of Rice with Variable Degrees of Resistance to RYMV The in vitro transcripts generated from the VIGS vectors, targeting the pds gene, were inoculated mechanically onto rice varieties with various degrees of resistance to RYMV: cv. IR64 spp. indica (sensitive), cv. Azucena spp. japonica (partially resistant), cv. Nipponbare spp. japonica, cv. Taipei309 spp. japonica) and transgenic lines (cv. Taipei309) (Pang et al. and Sallaud et al. above).

Each variety or line, four or five young plants (i.e. 15 days after sowing, two leaf-stage) were inoculated mechanically using carborundum. The inoculum corresponds to 20 µg of in vitro transcripts diluted two-fold into 20 mM of sodium phosphate buffer, pH 7.

Phenotypic characterization: visualization of the silencing phenotypes (gfp=disappearance of gfp under UV illumination, pds=bleaching of leaves).

Molecular characterization: extraction of total RNA (Trizol), polyacrylamide gel Northern blotting of low-molecular-weight RNAs and detection of siRNAs specific for the genes targeted by the VIGS.

serum directed against a Madagascar isolate, were bound beforehand to microtitration plates (Nunc) according to the procedure previously described (N'Guessan et al., 2000). Successive incubation and washing steps result in the detection of a positive reaction between the antigens deposited and the polyclonal antibody coupled to alkaline phosphatase. The reaction between alkaline phosphatase and its substrate, pNPP (p-nitrophenyl phosphatase substrate) (SIGMA®), diluted in a solution of diethanolamine (SIGMA®), generates a colored reaction whose intensity is measured by reading the optical density at 405 nm with a fluorimeter (Multiskan fluorimeter, Labsystem).

2a. Protein Extraction

The total water-soluble proteins are extracted from 100 mg of ground leaves, in a phosphate buffer (50 mM $NaHPO_4$, 10 mM $Na_2EDTA$, 1 mg·ml$^{-1}$ N-laurylsarcosine, 0.1% v/v triton), and the supernatant is recovered at the end of two successive centrifugations for 30 min at 20 000 g at 4° C. The proteins are assayed according to the Bradford method (Coomassie protein assay kit, Pierce) (Bradford, 1976). A standard range is produced by measuring the optical density at 595 nm obtained with known concentrations of BSA.

3a. Evaluation of Gus Activity by Histochemical Assay and Fluorimetric Assay

Two types of experiments are reported below, carried out in order to detect the enzymatic activity of β-glucuronidase (GUS). The histochemical assay on leaves was carried out as described in the literature (Jefferson et al., 1987) after infiltration under vacuum (15 min, 0.33 MPa) in the presence of 1 mg/ml$^{-1}$ X-GlucA (5-bromo-4-chloro-3-indolyl-β-D-glucuronide) (Duchefa) diluted in an appropriate buffer (50 mM sodium phosphate, 0.25 mM $K_3Fe(CN)_6$, 0.25 mM $K_4Fe(CN)_6$, 0.5% v/v Triton). The samples are then incubated for 12 h in the dark at 37° C. The leaves are then counterstained by treatment with a solution which destabilizes the chlorophyll (10% v/v of formaldehyde, 5% v/v of glacial acetic acid, 42.5% v/v of ethanol), for 24 h at ambient temperature. Finally, the leaves are rinsed several times and are stored in 70% (v/v) ethanol.

A fluorimetric assay of the Gus activity was carried out on the water-soluble proteins extracted from the systemically infected leaves. Five microliters of proteins were then subjected to the enzymatic assay for Gus activity in the presence of 1 mM of substrate (MUG (4-methylumbelliferyl-β-D-glucuronide), Sigma®) in a reaction volume of 200 µl. The kinetics of appearance of the fluorescent product of the enzymatic reaction (i.e. MU, excitation at 365 nm, emission at 455 nm) are realized for 2 h, with readings at intervals of 30 min, using a fluorimeter (Fluoroskan fluorimeter, Labsystem). A reference standard range is produced by measuring the fluorescence of various concentrations of MU. The enzymatic activity of Gus is expressed as amount of product synthesized per unit of time, and related back to the same amount of proteins: pmol MU/min/µg protein.

4a. RNA Analysis by Northern Blotting

The RNAs of the various samples were extracted from 100 mg of powder using Trizol® (Invitrogen™) according to the supplier's recommendations, and are taken up in 30 to 50 µl of 50% deionized formamide. The amount and the quality of the RNAs were respectively evaluated by measuring the optical density at 260 nm, and 2 µg of RNA were loaded onto a 1% agarose gel and migrated at 50 V/cm in 0.5×TBE.

Fifteen microgams of total RNA, complete after denaturation with ¼ of loading buffer (50% v/v glycerol, 50 mM Tris, pH 7.7, 5 mM EDTA, 0.03% v/v bromophenol blue) are separated by electrophoresis under denaturing conditions on a 17.5% polyacrylamide gel (7M urea, 17.5% v/v acrylamide-bisacrylamide 19:1, 0.5×TBE, 0.04% v/v Temed, 0.08% v/v ammonium persulfate) as previously described (Hamilton & Baulcombe, 1999), for 2 h at 100 V/cm in 0.5×TBE. The low-molecular-weight RNAs thus separated are electroblotted onto an uncharged nylon membrane (Hybond NX, Amersham) for 1 h at 100V at 4° C. in 0.5×TBE.

For the detection of siRNAs, the probe is labeled by random primer anchoring, using the Megaprime™ DNA labelling system kit (Amersham) in the presence of 20 U of Klenow and 5 µCi of α-$^{32}$P-dCTP in a reaction volume of 50 µl, according to the supplier's recommendations. The labeling is carried out for 1 h at 37° C. and the labeled probe is then purified on a Sephadex-G50 column (Amersham) before being denatured and incorporated into the hybridization buffer (PerfectHyb™ Plus hybridization buffer, Sigma®).

The probes used for the detection of miRNA are synthesized by phosphorylation of oligonucleotide primers (20 pmol) complementary to the miRNAs selected, with 10 units of T4 polynucleotide kinase (Qbiogene) in the presence of 2 µl of reaction buffer and 5 µCi of γ-$^{32}$P-dCTP, in a reaction volume of 20 µl. The labeling is carried out for 1 h at 37° C., and the labeled probe is purified on a Sephadex G25 column (Amersham) before being denatured and incorporated into the hybridization buffer.

The membranes are then hybridized overnight at the appropriate temperature (i.e. 42° C. for the detection of siRNA, Tm-20° C. for the detection of miRNA). Two successive washing steps of 20 min at 50° C. are then carried out with a solution of 2×SSC and 2% SDS. Finally, the membranes, wrapped in Saran Wrap, are exposed against an X-ray film (LifeRay™ XDA Plus, Ferrania imaging technologies) at −80° C. for a varying period depending on the desired signal strength. The X-ray film is revealed manually.

Once the membranes have been hybridized, they can be dehybridized by two successive treatments of 20 min with a solution of 0.1% SDS brought to boiling, for successive hybridization experiments.

B) Preparation of Constructs and Cloning

1b. Preparation of Vectors and Inserts

The vectors are prepared by digestion of the plasmid DNA with the appropriate enzyme in a reaction volume of 100 µl. The digestion products are then purified using the GFX™ PCR, DNA and Gel Band Purification kit (Amersham) according to the supplier's recommendations, and are taken up in 30 µl of elution buffer. The vectors digested with enzymes that generate blunt ends are treated with alkaline phosphatase. Thus, the entire purified digestion product is dephosphorylated using 1 U of CIP[1] (New England Biolabs) with 1×NEB3 buffer (New England Biolabs) in a reaction volume of 40 µl, for 1 h at 37° C. The dephosphorylated vectors are then purified on a GFX™ column (GFX™ PCR, DNA and Gel Band Purification kit, Amersham).

The inserts are PCR amplification products produced with a high-fidelity polymerase (Pfu, Promega) in a reaction volume of 50 µl. The PCR amplifications are carried out according to the supplier's recommendations, in the presence of its buffer (1×), of 200 µM of dNTP, of 0.5 µM of each primer and of 1.25 U of Taq. At the end of denaturation for 3 min at 95° C., the PCR cycles were carried out according to specific conditions: the anchoring of the primers to the template is carried out at the average Tm of the primers for 30 sec and the extension of the fragment is carried out at 72° C. for 1 min per kbp to be amplified; 30 amplification cycles were carried out. The PCR products of the expected size are then purified from an agarose gel on a GFX™ column (GFX™ PCR, DNA and Gel Band Purification kit, Amersham) and taken up in 30 µl of elution buffer. The inserts are then digested with the appropriate enzymes in a reaction volume of 40 µl. The digestion products are purified on a GFX™ column (GFX™ PCR, DNA and Gel Band Purification kit, Amersham).

The quality and the amount of the vectors and inserts are evaluated respectively by electrophoresis under nondenaturing conditions in 1×TAE and by measuring the optical density at 260 nm.

2b. Ligation

One hundred ng of vector were used for each ligation reaction, to which was added the desired amount of insert according to the formula: ng insert=ratio (insert/vector)×(ng vector×insert size)/vector size. Several types of vector/insert molecular ratios were used: 1:1, 1:3, 1:5. One and a half units of T4 DNA ligase (Invitrogen) with 2 µl of 5× ligase buffer (Invitrogen) were used for the various ligation reactions, carried out in a reaction volume of 10 µl for 20 h at 16° C.

3b. Transformation of Competent *Escherichia coli* (JM110, Promega)

Five microliters of ligation product are added to 50 µl of competent cells. After incubation for 10 min in ice, the bacteria are transformed by heat shock for 50 sec at 42° C. and are immediately returned to the ice for 2 min. Seven hundred microliters of cold SOC medium are then added to the cells, which are incubated for 1 h at 37° C. with shaking (225 rpm). The bacteria are then plated out by aliquots (i.e. from 50 to 300 µl) on selective medium (i.e. LB supplemented with 50 µg/ml$^{-1}$ of ampicillin) and the cultures are thus placed in an incubator overnight at 37° C.

The positive clones are validated by means of a PCR on the colonies.

4b. Preparation of *E. coli* Plasmid DNA

The bacteria (i.e. 20 µl of glycerolated culture or colony harvested using a platinum loop) are inoculated into 10 ml of selective LB medium. After an overnight culture at 37° C. with shaking (225 rpm), the cultures are centrifuged for 15 min at 4000 rpm and the plasmid DNA is extracted from the bacterial pellets using the GFX™ Micro plasmid prep kit (Amersham) according to the supplier's recommendations, and taken up in 60 µl of elution buffer.

5b. Electroporation of *Agrobacterium tumefaciens* (GV3101 Strain)

One to 2 µl of DNA are added to 40 µl of competent *agrobacteria*, which are then incubated for 2 min in ice. The integration of the plasmid DNA into the *agrobacteria* is then carried out by electroporation (Biorad Gene Pulser system) in a pre-cooled 4 mm tank, by application of an electrical discharge of 2.5 kV (25 µFa; 200 Ohms). One ml of cold SOC medium is then added to the cells, before incubating them for 3 h at 28° C. with shaking (225 rpm).

Aliquots of the transformation (i.e. 50 to 300 µl) are plated out on a selective medium (i.e. LB supplemented with 50 µg·ml$^{-1}$ rifampicin and 50 µg·ml$^{-1}$ kanamycin) and the cultures are thus incubated for 2 to 3 days at 28° C.

6b. Preparation of *A. tumefaciens* Plasmid DNA by Alkaline Lysis

The *agrobacteria* are inoculated into 10 ml of selective LB medium and cultured for 30 h (or more depending on the strain used) at 28° C. with shaking (225 rpm). The bacterial pellet obtained after centrifugation of the cells for 15 min at 4000 rpm is resuspended in 100 µl of 50 mM Tris, 10 mM EDTA, 100 µg·ml$^{-1}$ RNAse A and 5 mg·ml$^{-1}$ lysozyme. After incubation for 5 min in ice, 200 µl of lysis buffer are added (200 mM NaOH, 1% w/v SDS). The bacterial wall lysis is carried out for 4 min at 4° C. Finally, 200 µl of 3M sodium acetate (pH 5.5) are added and the mixture is centrifuged for 10 min at 13 000 rpm at 4° C., The DNA contained in the supernatant is precipitated with ethanol (1/10th v/v 3M NaAC, pH 5.5, 2 volumes 100% ethanol) for 30 min at −20° C. after two purification steps with phenol-chloroform. The precipitated DNA is pelleted by centrifugation for 45 min at 15 000 g at 4° C. After a step of washing with 70% ethanol, the DNA pellet is eluted in 60 µl of 1M Tris-HCl, pH 8.

C) Cell Biology Protocols

1c. Obtaining Tobacco (BY2) Protoplasts

The tobacco protoplasts are isolated from a culture of 2-to-3-day-old *Nicotiana tabaccum* BY2 cell suspensions. After 50 ml of cell suspensions have been separated by settling out for 20 min at ambient temperature, the supernatant is removed and replaced with 40 ml of 0.4M mannitol. The cells are plasmolyzed at the end of a 30-min incubation at ambient temperature, and the mannitol is then removed. A first protoplast isolation step is carried out by incubation of the plasmolyzed cells with 12.5 ml of enzymatic solution for 30 min at 28° C. with gentle shaking (55 rpm) in the dark. The cell aggregates are then dissociated by pipetting up and down 5 times successively using a plastic pasteur pipette. A second incubation is then carried out for 2 h at 28° C. with shaking (55 rpm) in the dark. The protoplasts thus obtained are centrifuged at 100 g for 15 min at 4° C. and the enzymatic solution is removed.

Before electroporation, 20 ml of 0.4M mannitol are added in order to maintain the protoplasts, which are kept in ice. The isolated protoplasts are then counted. The protoplasts are then centrifuged at 100 g for 15 min at 4° C. and taken up in an appropriate volume of 0.4M mannitol in order to obtain a density of $10^6$ protoplasts per ml; they are then kept in ice before electroporation.

1b. Obtaining Rice ($O_{2428}$) Protoplasts

The rice protoplasts are isolated from a culture of 3-to-5-day-old *O. sativa* $O_{2428}$ cell suspensions as previously described (Brugidou et al., 1995; Ndjiondjop et al., 2001) with a few modifications being introduced. After centrifugation for 10 min at 100 g, the supernatant is removed and replaced with 15 to 25 ml of PIS medium supplemented with 15 to 25 ml of R2 medium (while keeping a ratio of 1:1 of each medium) per 100 ml of sedimented cells. The protoplasts are thus isolated at the end of a 20 h incubation at 28° C. in the dark with gentle shaking (55 rpm). A few milliliters of CPW 13% MMa medium are then added to the solution of isolated protoplasts in order to facilitate the filtration of the protoplasts through a screen (50 µm). The filtered protoplasts are centrifuged for 10 min at 100 g at 4° C., and the supernatant is then removed and replaced with 15 ml of CPW 13% MMa in order to maintain the protoplasts kept in ice before electroporation. During counting of the protoplasts, the latter are sedimented by centrifugation for 10 min at 100 g at 4° C. and the pellets are taken up in the appropriate volume of CPW 0.04% MMA so as to obtain the desired protoplast density, and are kept in ice before electroporation.

1c. Protoplast Counting

The number and the viability of the protoplasts are evaluated by counting using a hemocytometer in the presence of trypan blue. The protoplasts (200 µl) are diluted to 1/5th in a solution of Hank's balanced salts (300 µl) (Sigma) and trypan blue (500 µl).

1d. Electroporation of Tobacco and Rice Protoplasts

An electroporation reaction is carried out by mixing 600 µl of electroporation medium with 200 µl of inoculum (i.e. 30 µg of in vitro transcript or 5 µg of plasmid DNA diluted in electroporation buffer) with protoplasts sedimented at the end of centrifugation (i.e. 5 min, 100 g, 40° C.) of 1 ml of isolated protoplasts. The mixture is subjected to an electrical discharge of 250 V (25 µFa, 200 Ohms) using the Biorad Gene Pulser system. After electroporation, the protoplasts are kept in ice for 30 min and at ambient temperature for 5 min and are centrifuged for 10 min at 100 g at 4° C. The supernatant is removed and replaced with an appropriate volume of protoplast culture medium (i.e. R2 medium for rice), and the protoplasts are then maintained for 7 days at 28° C. with shaking (90 rpm) in the dark.

D) Validation of the Viral Expression and VIGS Vector Constructs

1d. In Vitro Transcription

The plasmid DNA of the various constructs is linearized by restriction using the HindIII enzyme (i.e. 3' of the viral genome) followed by treatment for 1 h at 37° C. with 2 mg·ml$^{-1}$ of proteinase K. The linearized DNA is purified by two treatments with phenol/chloroform and precipitated with ethanol overnight at −20° C.

The in vitro transcription is carried out in a reaction volume of 100 µl, on 5 µg of linearized DNA in the presence of 10 mM DTT, 0.1 mg·ml$^{-1}$ BSA, 0.5 mM Cap analog structure (m$^7$G (5')ppp(5')G, New England Biolabs), rNTP (2 mM rATP, 200 µM rGTP, 2 mM rCTF, 2 mM rUTP), 80 U RNAsin (Promega), 100 U T7 RNA polymerase (Promega) with its reaction buffer. At the end of one hour of reaction at 37° C., 1 µl of transcripts is migrated on an agarose gel and 12 U of T7 RNA polymerase are added for a second hour of reaction.

At the end of the transcription, the quality and the amount of the transcripts are evaluated by migration on an agarose gel and by measuring the optical density at 260 nm.

2d. RNA Extraction

The RNAs of the various samples were extracted from 4 ml of protoplast culture (prior centrifugation for 10 min at 100 g) with 0.5 ml of TRIzol Reagent (Invitrogen™) according to the supplier's recommendations. The extracted RNAs are taken up in 10 µl of RNAse-free water.

The amount and the quality of the RNAs were respectively evaluated by measuring the optical density at 260 nm and by electrophoresis, under nondenaturing conditions, of 2 μg of RNA in 0.5×TBE at 50 V/cm.

3d. RT-PCR RNA Analysis

In order to do away with the bias from the amplification of the residual DNA template (i.e. at the end of the in vitro transcription) corresponding to the linearized recombinant vectors, a DNAse treatment is carried out on the RNAs. The effectiveness of the treatment is evaluated at the end of a PCR amplification on 2 μl of DNAse-treated RNA, using the same primers as those used for the validation of the recombinants.

Seven hundred and fifty nanograms of RNA are treated with 1 U of RQ1-DNAse (Promega) in the presence of its buffer in a reaction volume of 10 μl, for 30 min at 37° C. The reaction is stopped by the addition of 1 μl of care solution (Promega) followed by incubation for 5 min at 65° C. This treatment is carried out in duplicate on the samples, half will be used to evaluate the effectiveness of the treatment as described above, the other half is used to validate the vectors according to the approach which follows. The DNAse-treated RNAs are incubated for 5 min at 65° C. with 10 pmol of antisense primer (R20: 5' CTC CCC CAC CCA TCC CGA GA 3' (SEQ ID NO: 22) or oligodT) and 10 nmol of RNAse-free dNTP. In ice, a mixture of 1×RT buffer (Invitrogen), 10 mM DTT (Invitrogen) and 40 U of RNAse out (Invitrogen), is added to the previous mixture and incubated for 2 min at 42° C. Finally, 200 U of Superscript II (Invitrogen) are added to the reaction mixture. The complementary strand of the RNAs is synthesized at the end of an incubation for 50 min at 42° C., and the reaction is stopped after 15 min of incubation at 70° C. The samples are then treated with 100 U of RNase H (Invitrogen) for 30 min at 37° C.

At the end of the reverse transcription reaction, a PCR is carried out on 2.5 or 5 μl of the samples in a 12.5 μl reaction volume (or 5 μl of RT in a final volume of 15 μl) in the presence of 2 mM $MgCl_2$, 0.2 mM dNTP, 0.1 μM of each primer, 0.02 U of DNA polymerase (Interchim), and 1× of amplification buffer. The amplification program begins with a denaturation for 3 min at 94° C., then 30 amplification cycles are carried out (denaturation for 45 sec at 94° C., hybridization for 30 sec at the average Tm of the primers used, extension for 1 min per kbp to be amplified at 72° C.), and a final extension step of 5 min at 72° C. ends the amplification reaction.

Ten microliters of the amplification products are separated by electrophoresis under nondenaturing conditions, on an agarose gel in 1×TAE, at 100 V/cm.

4d. Protein Analysis by Western Blotting

Protein Separation

Ten micrograms of proteins are mixed with ¼ of loading buffer and denatured for 15 min at 100° C. The proteins are then separated under denaturing conditions on a 12.5% SDS-PAGE gel. The electrophoresis is carried out in two steps in an appropriate migration buffer:
- the samples are concentrated in the first part of the gel (i.e. stacking) by a migration at 80 V/cm.
- they are then separated at the end of a migration for 3 to 4 h (i.e. until the blue color from the loading buffer leaves the gel) at 100 V/cm.

Electroblotting

At the end of the migration, the proteins are electroblotted onto a 0.45 μm nitrocellulose membrane (Trans-Blot® Transfer Medium, Biorad) by applying an electric current of 100 V for 1 h or of 20 V overnight at 4° C.

Immunodetection

All the incubation and washing steps are carried out at ambient temperature with shaking, using a platform shaker, at variable speeds of 20-25 rpm and 45-50 rpm for the incubation and washing steps respectively.

The membrane is incubated for 1 h in a blocking solution containing TBSt and 0.5% w/v of BSA (immunodetection with monoclonal antibodies) or 3% w/v of non-fat dry milk (Biorad) (immunodetection with polyclonal antibodies). The membrane is then incubated for 1 h with the first antibody diluted to 1/1000th in the same blocking solution. The monoclonal antibody used, Mab E, was obtained using an epitope of RYMV, whereas the solution of polyclonal antibodies, Pab Mali, was obtained using the whole viral particle of a Mali isolate. The membrane is then rinsed by means of 6 successive washes for 5 min with TBSt, then incubated for 1 h with the second antibody (anti-mouse IgG or anti-rabbit IgG, coupled to peroxidase, in order to reveal, respectively, serological reactions with monoclonal or polyclonal antibodies) diluted to 1/40 000th in a new blocking solution. Six successive washes of the membrane, for 5 min in TBSt, are then carried out. The antigen-antibody interaction is revealed by chemiluminescence, and the excitation is brought about using a chemical reaction with peroxidase in the presence of a West Pico solution (Pierce) applied to the membrane and incubated for 5 min in the light. The membrane wrapped in Saran Wrap is then exposed to an X-ray film (CL-X Posure™ Film, Pierce) at ambient temperature for a varying period depending on the desired signal strength. The X-rayed film was revealed manually.

Molecular Biology Buffers

10×TBE: 0.9M Tris-borate, 20 mM EDTA

50×TAE: 2M Tris-acetate, 50 mM EDTA

Buffers and Solutions for Western Blotting

Separating gel: 12% acrylamide-bisacrylamide (29:1), 0.4M Tris HCl, pH 8.8, 0.1% SDS, 0.1% ammonium persulfate, 0.1% Temed.

Stacking gel: 5% acrylamide-bisacrylamide (29:1), 125 mM Tris HCl, pH 6.8, 0.1% SDS, 0.1% ammonium persulfate, 0.1% Temed.

Migration buffer: 25 mM Tris base, 0.25M glycine, 0.1% SDS.

Blotting buffer: 20 mM Tris base, 0.15M glycine, 2% methanol.

4× loading buffer: 200 mM Tris HCl, pH 6.8, 400 mM DTT, 8% SDS, 0.4% bromophenol blue, 40% glycerol.

TBS, pH 7.5: 20 mM Tris base, 75 mM NaCl, 2.5 mM $MgCl_2$.

TBS-t: TBS, 0.05% Tween 20.

Cell and Bacterial Culture Media

LB (pH 7): 10 $g \cdot l^{-1}$ tryptone, 5 $g \cdot l^{-1}$ yeast extract, 10 $g \cdot l^{-1}$ NaCl.

SOC: 20 $g \cdot l^{-1}$ tryptone, 5 g/L yeast extract, 0.5 $g \cdot l^{-1}$ NaCl, 2.5 mM KCl (pH 7).

Sterile glucose (20 mM) is added to the medium after autoclaving.

Cell Culture Media

BY2 tobacco cells

Maintenance of Tobacco Suspensions (pH 5.8):

4.3 $g \cdot l^{-1}$ MS salts (Duchefa M0221), 1 $mg \cdot l^{-1}$ thiamine HCl, 100 $mg \cdot l^{-1}$ myoinositol, 30 $g \cdot l^{-1}$ sucrose, 0.2 $mg \cdot l^{-1}$ 2,4-D Protoplast Culture Medium (pH 5.8):

4.3 $g \cdot l^{-1}$ MS salts (Duchefa M0221), 1 $mg \cdot l^{-1}$ thiamine HCl, 100 $mg \cdot l^{-1}$ myoinositol, 10 $g \cdot l^{-1}$ sucrose, 0.4M D-mannitol, 0.2 $mg \cdot l^{-1}$ 2,4-D Enzymatic Solution for Protoplast Preparation (pH 5.5):

1% cellulase Onozuka RS, 0.1% pectolyase Y-23, 0.4M D-mannitol. The solution is sterilized by filtration through 0.22 μm and aliquoted in volumes of 25 ml. Storage at −20° C.

Protoplast Electroporation Medium (pH 5.8):

0.3M mannitol, 70 mM KCl, 5 mM MES.

$O_{2428}$ rice cells

PIS Medium (Enzymatic Solution for Protoplast Preparation) (pH 6):

2% cellulase RS, 0.1% pectolyase Y23. The enzymes are diluted in CPW 13% MMa and sterilized by filtration to 0.22 μm. The solution is stored at −20° C.

CPW 13% MMa Medium (Protoplasts):

100× solution: 20 mM $KH_2PO_4$, 0.1M $KNO_3$, 0.2M $MgSO_4$ CPW 13% MMa (pH 5.8): 10 ml/l 100× solution, 10 mg/ml KI, 10 mg/ml $CuSO_4.5H_2O$, 5 mM MES, 10 mM $CaCl_2$, 0.7M mannitol. The solution should be stored at −20° C.

CPW 0.04% MMa Medium (Protoplasts):

The medium has the same composition as the CPW 13% MMa medium, only the mannitol concentration varies: 0.4M.

R2 Media (Protoplasts):

Macroelements R2-I (10×): 40 g·l$^{-1}$ $KNO_3$, 3.3 g·l$^{-1}$ $(NH_4)_2SO_4$, 3.12 g·l$^{-1}$ $NaH_2PO_4.H_2O$, 10 mM $MgSO_4$.

Macroelements R2-II (10×): 1.46 g·l$^{-1}$ $CaCl_2.2H_2O$.

Microelements R2 (1000×): 1.6 g·l$^{-1}$ $MnSO_4.H_2O$, 2.2 g·l$^{-1}$ $ZnSO_4.7H_2O$, 2.83 g·l$^{-1}$ $H_3BO_3$, 0.125 g·l$^{-1}$ $CuSO_4.5H_2O$, 0.125 g·l$^{-1}$ $Na_2MoO_4.2H_2O$.

Vitamins R2 (40×): 40 mg·l$^{-1}$ thiamine HCl.

FeNaEDTA (100×): 1.25 g·l$^{-1}$ $FeSO_4.7H_2O$, 0.5 mM $Na_2EDTA$.

R2 medium (pH 5.8): IX macroelements R2-I, 1× macroelements R2-II (1×), 1× microelements R2, 1× vitamins R2 (1×), 1× FeNaEDTA, 2.5 mg·l$^{-1}$, 2.4-D, 0.4M maltose, 0.5 mg·l$^{-1}$ nicotinic acid, 100 mg·l$^{-1}$ myoinositol, 0.5 mg·l$^{-1}$ pyrodoxine.

BIBLIOGRAPHICAL REFERENCES

Bradford, M. (1976). A rapid and sensitive method for quantification of microgram quantities of protein utilising the principle of protein-dye binding. *Annal of Biochemestry* 72, 248-254.

Brugidou, C., Holt, C., Yassi, M. N., S., Z., Beachy, R. N. and Fauquet, C. (1995). Synthesis of an infectious full-length cDNA clone of Rice yellow mottle virus and mutagenesis of the coat protein. *Virology* 206, 108-115.

Hacker, D. L. and Sivakumarann, K (1997). Mapping and expression of *Southern Bean mosaic virus* genomic and sub-genomic RNAs. *Virology* 234, 317-327.

Hamilton, A. J. and Baulcombe, D. C. (1999). A Species of Small Antisense RNA in Posttranscriptional Gene Silencing in Plants. *Science* 286, 950-951.

Pang, S. Z., DeBoer, D. L., Wan, Y., Ye, G., Layton, J. G., Neher, M. K., Armstrong, C. L., Fry, J. E., Hinchee, M. and Fromm, M. E. (1996). An Improved Green Fluorescent Protein Gene as a Vital Marker in Plants. *Plant Physiology* 112, 893-900.

Sallaud, C., Mcynard, D., van Boxtel, J., Gay, C., Bès, M., Brizard, J. P., Larmande, P., Ortega, D., Raynal, M., Portefaix, M. et al. (2003). Highly efficient production and characterization of T-DNA plants for rice (*Oryza sativa* L.) functional genomics. *Theoretical and Applied Genetics* 106, 1396-1408.

What is claimed is:

1. A method of selecting RYMV (Rice Yellow Mottle Virus) P1 proteins having PTGS (Post Transcriptional Gene Silencing) suppressor activity, said method comprising:
   cloning genes encoding RYMV P1 proteins downstream of a RYMV 35S promoter to form expression cassettes, said expression cassettes containing a GUS reporter gene,
   inoculating the expression cassettes encoding the suppressor proteins by biolistics onto rice leaves,
   mechanically inoculating RYMV virus into said rice leaves,
   assaying the viral load by DAS-ELISA using a polyclonal antibody directed against the virus,
   visualizing the restoration of expression of the GUS reporter gene encoding beta-glucoronidase by histochemical assay,
   quantifying the restoration of expression of the GUS reporter gene by assaying the enzymatic activity of GUS,
   detecting siRNAs as evidence of PTGS by Northern blotting, and
   selecting P1 proteins having PTGS suppressor activity.

2. The method of claim 1, wherein the RYMV P1 protein is selected from a Tz3 RYMV isolate, a Tz8 RYMV isolate, an Mg1 RYMV isolate, and an CI63 RYMV isolate.

3. The method of claim 2, wherein the RYMV P1 protein is a CI63 RYMV isolate or a Tz3 RYMV isolate.

4. The method of claim 2, wherein the Tz8 P1 protein is selected for an intermediate level of effectiveness for PTGS suppression, and the Mg1 P1 protein is selected for a low level of effectiveness in PTGS suppression.

5. A viral vector, comprising a gene encoding a RYMV P1 protein selected from a Tz3 RYMV isolate, a Tz8 RYMV isolate, an Mg1 RYMV isolate, and an CI63 RYMV isolate, wherein said vector is a virus induced gene silencing (VIGS) vector and contains an insert of less than 50 bp in size, said insert being inserted in said vector in sense or antisense orientation, the target of said insert being a host mRNA transcript.

6. A viral vector, comprising a gene encoding a RYMV P1 protein selected from a Tz3 RYMV isolate, a Tz8 RYMV isolate, an Mg1 RYMV isolate, and an CI63 RYMV isolate, wherein said vector is a viral protein expression vector and contains an insert of greater than 700 bp of a gene of interest to be overexpressed, said insert being inserted into the replicative ORF 2a and 2b of RYMV.

* * * * *